United States Patent [19]

Batorewicz

[11] 3,945,954

[45] Mar. 23, 1976

[54] FLAME RETARDANT POLYURETHANES FROM POLYMERIC HALOGENATED ORGANO PHOSPHOROUS DIOLS

[75] Inventor: Wadim Batorewicz, New Haven, Conn.

[73] Assignee: Uniroyal, Inc., New York, N.Y.

[22] Filed: Oct. 31, 1974

[21] Appl. No.: 519,441

Related U.S. Application Data

[62] Division of Ser. No. 432,703, Jan. 11, 1974, Pat. No. 3,882,199.

[52] U.S. Cl. 260/2.5 AR; 260/2.5 AJ; 260/77.5 AR
[51] Int. Cl.$^2$.................. C08G 18/14; C08G 18/32
[58] Field of Search.. 260/2.5 AR, 2.5 AJ, 77.5 AR, 260/75 NR

[56] References Cited
UNITED STATES PATENTS

| | | | |
|---|---|---|---|
| 3,157,613 | 11/1964 | Anderson | 260/2.5 AJ |
| 3,192,242 | 6/1965 | Birum | 260/927 R |
| 3,262,999 | 7/1966 | Friedman | 260/2.5 AR |
| 3,423,486 | 1/1969 | Rätz | 260/2.5 AR |

*Primary Examiner*—Donald E. Czaja
*Assistant Examiner*—C. Warren Ivy
*Attorney, Agent, or Firm*—Robert J. Patterson

[57] ABSTRACT

Polymeric halogenated organophosphorus diols are obtained by reacting chlorine or bromine with spirocyclic phosphites and thereafter reacting the halogenated product with a diol, in the presence of an acid acceptor. These novel viscous polymers react with polyisocyantes to produce polyurethanes. Polyurethanes so made are characterized by improved flame retardant properties compared with conventional polyurethanes. Such polyurethanes are preferably in the form of foams, especially flexible foams.

3 Claims, No Drawings

FLAME RETARDANT POLYURETHANES FROM POLYMERIC HALOGENATED ORGANO PHOSPHOROUS DIOLS

This is a division of application Ser. No. 432,703 filed Jan. 11, 1974, now U.S. Pat. No. 3,882,199.

BACKGROUND OF THE INVENTION

The invention relates to polymeric halogenated organophosphorus diols. More particularly, the invention relates to processes for preparing these novel polymeric materials and utilizing the same along with other polyols, as co-reactants in the production of polyurethanes. Polyurethanes containing these novel polymeric materials have superior flame retardant properties when compared to conventional polyurethanes.

Organophosphorus compounds containing halogens are well known in the art. Many compositions of this broad class of materials have been claimed as flame retardants for a variety of polymers, including polyurethanes. A substantial portion of such materials are of the additive type. That is, these materials are not chemically bound to the polymer backbone. Such additive flame retardants are described, for example, in the U.S. Pat. No. 3,192,242. The organophosphorus materials disclosed in this patent have the general formula:

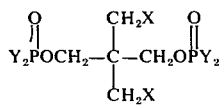

wherein X is a halogen such as bromine or chlorine and Y is a haloalkoxy group.

Reactive type flame retardants usually possess at least two reactive sites through which they are chemically bound to the polymer backbone. These retardants are superior to the additive type retardants, because not only will they not evaporate, sublime or leach out of the polymer substrate during use or processing but they also form an integral part of the polymer structure.

Reactive type flame retardants such as chlorine containing phosphate polyols have been employed to improve polyurethane resins. These reactive flame retardants are typified in U.S. Pat. No. 3,423,486.

While various known reactive type flame retardants are useful in rigid type polyurethane foam, they may not be employed advantageously in the production of flexible type foam. For example, the above mentioned phosphate polyols are tetrafunctional monomers, that is they possess large OH Numbers, and this characteristic makes them unsuitable as correactants in a flexible foam formulation which requires polyols having a functionality in the range from 2 to 2.5, as well as an OH number of 100 of preferably less.

The polymeric halogenated organophosphorus diols of the invention are prepared by chlorinating or brominating a spirocyclic phosphite at temperatures from about −50°C. to +50°C, and condensing halogenated reaction product with a diol in the presence of an acid acceptor. These novel diols possess hydroxyl groups capable of forming urethane linkages with isocyanates. Although the diols of the invention may be used alone with polyisocyanates to form polyurethane-type polymers they may also be employed in admixture with other suitable polyols.

The novel compositions of this invention are especially useful in the production of flexible urethane foams. It was found that these polymeric diols can be incorporated into the foam in amounts sufficient to render the foam flame-resistant without significantly affecting physical properties of the polymer substrate.

DESCRIPTION OF THE PREFERRED EMBODIMENTS

Polymeric halogenated organophosphorus diols of the invention are represented by general formula I

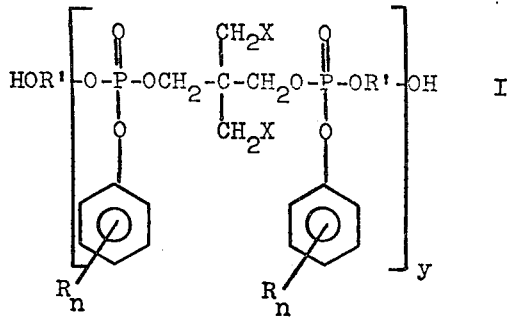

wherein R may be:
a. hydrogen, chlorine or bromine;
b. an alkyl, haloalkyl or alkoxy radical having from one to six carbon atoms;

wherein n may vary from 1 to 3;

wherein R' may be:
c. a branched or linear alkylene, alkenylene, alkynylene or alkoxyalkylene radical containing from two to ten carbon atoms; optionally containing bromine or chlorine substituents.

wherein X may be chlorine or bromine; and
wherein y typically has a value of from 1 to 5 but not more than 7.

Those skilled in the art will appreciate that y denotes an average value and that particularly within polymers having a broad molecular weight distribution species having y values somewhat greater than 5, e.g., as high as 7, are possible. The diols of general formula I are prepared from spirocyclic compounds of general formula

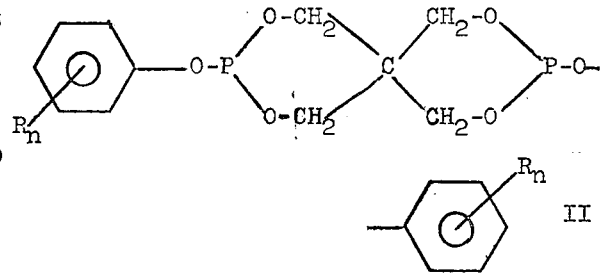

The above compounds may be prepared according to U.S. Pat. No. 2,847,443.

While any of the spirocyclic phosphites containing aryl type substituents in the 3,9 position may be used, the preferred spirocyclic phosphites in the context of this invention are 3,9-bis(phenoxy)-2,4,8,10-tetraoxa-3,9-diphosphaspiro [5.5] undecane and 3,9-bis(p-bromo-phenoxy)-2,4,8,10-tetraoxa-3,9-diphosphaspiro [5.5] undecane.

Chlorine or bromine is added to the spirocyclic phosphite of structure II at atmospheric pressure to produce a halogen-containing Arbuzov type rearrangement product characterized by the phosphorohalidate of structure III.

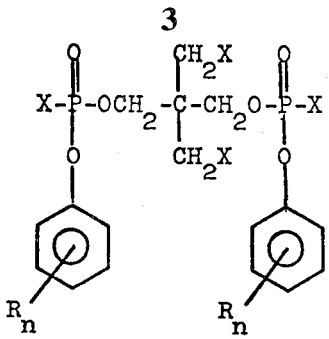

III wherein R, X and *n* have the meanings shown above. This reaction requires external cooling during the stepwise addition of the halogen in order to maintain temperatures preferably, from about −20°C. to +20°C; however, −50°C. to +50°C. is operable. The intermediate phosphorohalidate is substantially free of by-products and is conveniently prepared in situ before the subsequent reaction with a diol.

The addition of the phosphorohalidate of structure III to the appropriate diol in the presence of an acid acceptor such as a tertiary amine produces the polymeric halogenated organophosphorus diols of structure I. This reaction is preferably carried out in the presence of an acid acceptor such as a tertiary amine, for instance triethylamine, tripropylamine, pyridine, diethylaniline and others, in order to tie up hydrogen halide liberated during the reaction, by forming the respective amine hydrohalide salt.

The amine salt by-product of the reaction is removed by filtration and the filtrate is extracted with water to remove any residual amine salt. The organic phase is then concentrated under reduced pressure to remove any unreacted amines and diols. The polymeric halogenated phosphate ester diol product remains as a pot residue.

A wide variety of inert organic solvents can be used advantageously in this reaction. It is preferable, but not essential, to select a solvent in which all reactants are soluble; especially the more insoluble diols. For example, benzene can be employed with triethylene glycol; chloroform with 1,2-propanediol or dipropylene glycol; and acetonitrile with ethylene glycol which is insoluble in the above-mentioned solvents.

Molar ratios of the diols per mole of the phosphite can vary from 1.5 moles to 2.0 moles of diol per mole of phosphite. The preferred ratio is 2:1. However, when a large excess of a diol is used, the unreacted portion of the diol may be removed by distillation, generally under reduced pressure.

A great variety of diols can be employed in the preparation of the novel compositions of this invention. Preferred are diols including ethylene glycol, diethylene glycol, triethylene glycol, 1,2- or 1,3 propylene glycol, dipropylene glycol and tripropylene glycol. Other diols useful for the production of compounds of this invention include aliphatic diols containing from three to about ten carbon atoms. These diols may be linear or branched and may bear either all primary or all secondary OH groups or a mixture of primary and secondary OH groups. The polyols may also contain unsaturation or halogen substituents. Exemplary are diols such as 2-butenediol-1,4, 2-butynediol-1,4, 2,3-dibromo-1,4-butanediol, 2,3-dichloro-1,4-butanediol, 2,3-dibromo-2-butenediol-1,4, 3-bromo-1,2-propanediol, 3-chloro-1,2-propanediol, 2,2-bis(bromomethyl)-1,3-propanediol, and 2,2-bis(chloromethyl)-1,3-propanediol, and the like. Higher molecular weight diols, such as, polyethylene ether glycols and polypropylene ether glycols may also be used in the invention.

There is no advantage in employing high functionality polyols such as triols, tetrols, hexols and the like because the products derived from such polyols will possess high viscosity, functionality greater than two and large OH Numbers. These properties will render the products unsuitable as coreactants in a flexible urethane foam formulation where low viscosity, and functionality between 2 and 2.5 as well as OH Numbers of 100 or less are sought.

The polymeric halogenated organophosphorus diols according to the invention are oily materials which are neutral to moist litmus. These polymers are soluble in polyether polyols normally employed in polyurethane production as well as most common organic solvents. Good solubility renders the polymers of this invention especially useful in polyurethane foams where homogeneity and low viscosity of the polyol components are important.

The invention will now be described by reference to specific examples; however, in no way should these specific examples be interpreted as limiting the scope of the present invention.

EXAMPLE 1

Chlorine gas is passed through a solution of 3,9-bis(-phenoxy)-2,4,8,10-tetraoxa-3,9-diphosphaspiro [5.5] undecane (150 g., 0.42 moles) in benzene (500 ml.), for a period of five hours. During the addition the temperature of the solution is kept below 25°C by means of an ice-water bath. Following addition, the pale yellow colored solution is concentrated to about one-half volume under aspirator pressure and then added dropwise with stirring to a benzene solution (800 ml.) of triethylene glycol (180 g., 1.20 moles) and triethylamine (83.0 g., 0.79 moles); thereby causing a slow temperature rise to about 50° to 60°C. The resulting mixture is refluxed for four hours and kept overnight. Thereafter the amine salt is separated by filtration and the filtrate is first concentrated under an aspirator pressure and then under about 0.3 mm pressure of Hg at 125 to 135°C pot temperature to remove the excess glycol. The resulting polymeric diol is a brown oil, which is neutral to moist litmus.

Analysis: OH Number 108; 8.43%P; 9.11%Cl; y = 1.9 (average)

EXAMPLE 2

A solution of bromine (85.0 g, 0.53 mole) in chloroform (100 ml.) is added dropwise with stirring to a solution of 3,9-bis(phenoxy)-2,4,8,10-tetraoxa-3,9-diphosphaspiro [5.5] undecane (100 g., 0.26 moles) in chloroform (200 ml.). During the addition the temperature of the reaction solution is kept at about 5° to 10°C. by means of an ice-water bath. Upon completion of the addition reaction the solution acquired a permanent brownish color.

This brownish colored solution is added dropwise with stirring to a solution of ethylene glycol (76.0 g., 1.23 moles) and triethylamine (128 g., 1.22 moles) in acetonitrile (400 ml.); thereby causing a slow temperature rise. The resulting solution is kept under reflux for one hour and then concentrated under an aspirator pressure.

The residue is diluted with chloroform (800 ml.) and then washed with two 300 ml. portions of water prior to drying over anhydrous sodium sulfate.

The chloroform solution is then concentrated under an aspirator pressure and finally under about 0.5 mm pressure of Hg at 50° to 70°C pot temperature. The polymeric diol obtained is a dark tan oil which is neutral to moist litmus.

Analysis: OH Number 67; 7.62%P; 25.87% Br; $y = 2.7$ (average)

EXAMPLE 3

A solution of 3,9-bis(phenoxy)-2,4,8,10-tetraoxa-3,9-diphosphaspiro [5.5] undecane (100 g., 0.26 mole) in chloroform (200 ml) is treated with bromine as in Example 2. The resulting brownish solution is added dropwise with stirring to a solution of triethylene glycol (239 g., 1.59 moles) and triethylamine (111 g., 106 moles) in chloroform (400 ml.); thereby causing a slow temperature rise to 40°C. The resulting solution is kept under reflux for three hours and then allowed to stand overnight. Then, the reaction solution is diluted with chloroform (300 ml.); washed with diluted hydrochloric acid; washed with sodium carbonate solution; and finally washed with water. The chloroform phase is dried over anhydrous sodium sulfate and then concentrated under aspirator pressure and then under about 0.5 mm pressure of Hg at 50° to 70°C. pot temperature.

The polymeric diol obtained is a light tan oil.

Analysis: OH Number 89; 7.97%P; 19.86% Br; $y = 1.6$ (average)

EXAMPLE 4

A solution of 3,9-bis(p-bromophenoxy)-2,4,8,10-tetraoxa-3,9-diphosphaspiro[5.5] undecane (114.0 g., 0.21 mole) in chloroform (250 ml.) is treated with bromine as in Example 2. The resulting colored solution is added dropwise with stirring to a solution of 1,2-propanediol (32.0 g., 0.42 mole) and triethylamine (43.0 g., 0.42 mole) in chloroform (300 ml.); thereby causing a mild exotherm.

The resulting solution is refluxed for two hours; washed with two 250 ml. portions of water; and dried over anhydrous sodium sulfate. Then, the solution is concentrated, first under aspirator pressure and finally under about 0.1 mm. pressure of Hg at about 100°C. pot temperature.

The polymeric diol obtained is a viscous tan oil (131.0 g.) which is neutral to moist litmus.

Analysis: OH number 44; 7.02%P; 40.42% Br. $y = 4$(average)

EXAMPLE 5

A solution of 3,9-bis(phenoxy)-2,4,8,10-tetraoxa-3,9-diphosphaspiro [5.5] undecane (280.0 g., 0.74 mole) in chloroform (600 ml.) is treated with bromine as in Example 2. The resulting brownish solution is concentrated under an aspirator pressure to about 450 ml. and added dropwise with stirring to a solution of dipropylene glycol (200.0 g., 1.48 moles) and triethylamine (152.0 g., 1.51 moles) in chloroform (800 ml.); thereby causing a gradual rise in temperature to about 55°C.

The resulting solution is refluxed for two hours; washed with two 250 ml. portions of water and dried over anhydrous sodium sulfate. Then, the solution is first concentrated under an aspirator pressure and finally under about 0.1 to 0.3 mm. pressure of Hg at about 100°C pot temperature.

The polymeric diol produced (498 g.) is a tan oil which is neutral to moist litmus.

Analysis: OH Number 58; 8.75%P; 20.39%Br; $y = 2.6$(average)

It will be obvious that in the products made according to the foregoing specific examples the group R' has the structure indicated below:

| Example(s) | R'(diol residue) |
|---|---|
| 1 and 3 | $-CH_2CH_2-O-CH_2CH_2-O-CH_2CH_2-$ |
| 2 | $-CH_2CH_2-$ |
| 4 | $-CH_2\underset{\underset{CH_3}{\mid}}{\overset{\overset{H}{\mid}}{C}}-$ |
| 5 | $-\underset{\underset{CH_3}{\mid}}{C}HCH_2-O-CH_2\underset{\underset{CH_3}{\mid}}{C}H-$ |

EXAMPLE 6

This example illustrates the utility of the polymeric polyol compositions in the production of flame-retardant polyurethane foams.

Stannous octoate (0.3 g.; M&T, T-9 (trademark)) an amine type catalyst (0.3 g.; Houdry, Dabco 33-LV (trademark)), a silicone surfactant (4.0 g.; Union Carbide, L-520 (trademark)), and water (6.4 g.) are combined with a solution of a polyether polyol having an OH number of 48.5 and a molecular weight of about 3500 (158 g.; Union Carbide, 1446 Polyol (trademark)), and the phosphate ester diol having an OH Number of 58.1 (42 g.; prepared as in Example 5).

The above ingredients are thoroughly mixed and combined with toluene diisocyanate (76.2 g., an 80:20 mixture of 2,4-and 2,6-isomers). The resulting foam is subjected to a 10 minute post cure cycle at 100°C. A foam having fine open cells and excellent resilience is obtained.

The foam thus produced is rated as self-extinguishing utilizing the ASTM D-1692 flammability test.

A comparison foam prepared as described above but using the conventional polyether polyol instead of the polymeric diol of Example 5 was tested and rated as burning by the same test.

What is claimed is:

1. A flame retardant polyurethane material resulting from the interaction of an organic polyisocyanate and a polyol material comprising a polymeric organophosphorus ester diol having the structure

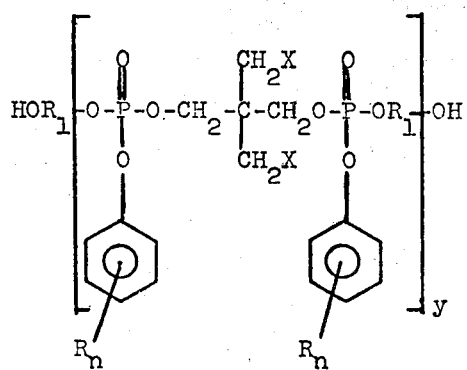

wherein R may be:
  a. hydrogen, chlorine, or bromine;
  b. an alkyl, haloalkyl, or alkoxy radical having from one to six carbon atoms;

wherein $n$ may vary from 1 to 3; wherein $R_1$ may be: a branched or linear alkylene, alkenylene, alkynylene or alkoxyalkylene radical containing from two to ten carbon atoms, optionally containing bromine or chlorine substituents; wherein X may be chlorine or bromine; and wherein $y$ has a value of from 1 to 7.

2. A flame retardant polyurethane material as set forth in claim 1, said polyurethane material being a foam.

3. A flame retardant polyurethane material as set forth in claim 1, said polyurethane material being a flexible foam.